United States Patent [19]

Herter et al.

[11] Patent Number: 4,954,501

[45] Date of Patent: Sep. 4, 1990

[54] PIPERAZINE SUBSTITUTED 6-PHENYLDIHYDRO-3(2H)-PYRIDAZI-NONES, AND PHARMACEUTICAL PREPARATIONS CONTAINING THESE

[75] Inventors: Rolf Herter, Schwabach; Peter Mörsdorf, Langenzenn; Volker Pfahlert, Nuremberg; Heidrun Engler, Cadolzburg; Helmut Schickaneder, Eckental; Kurt-Henning Ahrens, Nuremberg, all of Fed. Rep. of Germany

[73] Assignee: Heumann Pharma GmbH & Co., Nuremberg, Fed. Rep. of Germany

[21] Appl. No.: 247,868

[22] Filed: Sep. 21, 1988

[30] Foreign Application Priority Data

Feb. 12, 1988 [DE] Fed. Rep. of Germany ....... 3804490

[51] Int. Cl.$^5$ ..................... A61K 31/50; C07D 237/06
[52] U.S. Cl. ..................... 514/252; 514/247; 540/575; 544/114; 544/238; 544/239
[58] Field of Search ............... 514/252, 247; 544/239, 544/238

[56] References Cited

U.S. PATENT DOCUMENTS

| | | | |
|---|---|---|---|
| 4,088,762 | 5/1978 | Hakim | 544/238 |
| 4,521,415 | 6/1985 | Katakami | 514/252 |
| 4,584,299 | 4/1986 | Steffen et al. | 514/252 |
| 4,624,951 | 11/1986 | Göschke | 544/114 |
| 4,636,504 | 1/1987 | Rossy et al. | 514/252 |
| 4,666,902 | 5/1987 | Zoller et al. | 514/252 |
| 4,710,496 | 12/1987 | Geiss et al. | 514/252 |
| 4,820,697 | 4/1989 | Sircar et al. | 544/238 |

FOREIGN PATENT DOCUMENTS

| | | |
|---|---|---|
| 0075436 | 4/1986 | European Pat. Off. . |
| 0186484 | 7/1986 | European Pat. Off. . |
| 0249835 | 3/1988 | European Pat. Off. ............ 544/239 |
| 0304534 | 3/1989 | European Pat. Off. . |
| 2150436 | 4/1972 | Fed. Rep. of Germany . |
| 2207517 | 12/1972 | Fed. Rep. of Germany . |
| 2837161 | 3/1980 | Fed. Rep. of Germany . |
| 0146570 | 9/1983 | Japan ................ 544/239 |
| 0218666 | 9/1988 | Japan ................ 544/238 |

*Primary Examiner*—Donald G. Daus
*Attorney, Agent, or Firm*—Burns, Doane, Swecker & Mathis

[57] ABSTRACT

New 6-phenyldihydro-3(2H)-pyridazinones corresponding to the following general formula

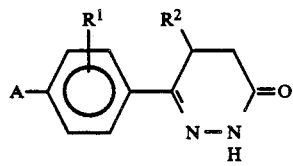

are described. These compounds are readily prepared in a form suitable for oral administration and are distinguished by a high positive inotropic action and have only a slight effect on blood pressure and cardiac frequency. A process for their preparation and pharmaceutical preparations containing these compounds are also described.

7 Claims, No Drawings

PIPERAZINE SUBSTITUTED 6-PHENYLDIHYDRO-3(2H)-PYRIDAZINONES, AND PHARMACEUTICAL PREPARATIONS CONTAINING THESE

DESCRIPTION

Digitalis glycosides such as digoxin and digitoxin and sympathomimetic drugs have for many years been the only medicaments available for the treatment of cardiac insufficiency. The disadvantages of these substances, such as their undesirable chronotropic and arrhythmogenic side effects, tachyphylaxis and, in the case of the sympathomimetic drugs, their lack of availability in a form suitable for oral administration, led to an intensive search for new classes of compounds having a positive inotropic action.

In the course of this search, substances with a positive inotropic action have been found in the series of 3(2H)-pyridazinones, as, for example, pimobendane (DE-OS 28 37 161) or imazodane (EP-OS 0 075 436).

On the other hand, some substituted 6-phenyl-3(2H)-pyridazinones have only been described as having antihypertensive or antithrombotic actions (DE-OS 21 50 436, DE-OS 22 07 517, U.S. Pat. No. 4,624,951).

It was an object of the present invention to provide new substituted 6-phenyldihydro-3-(2H)-pyridazinones which would combine a satisfactory antihypertensive action with a highly positive inotropic action and would be obtainable in a suitable form for oral administration.

This invention relates to substituted 6-phenyldihydro-3(2H)-pyridazinones corresponding to the general formula I

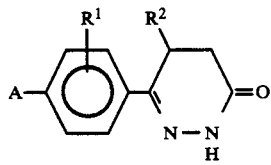

wherein
R$^1$ denotes a nitro group, an amino group, a hydroxyl group, a cyano group or a halogen atom,
R$^2$ stands for a hydrogen atom, a methyl group or a hydroxymethyl group and
A stands for a group of the formula

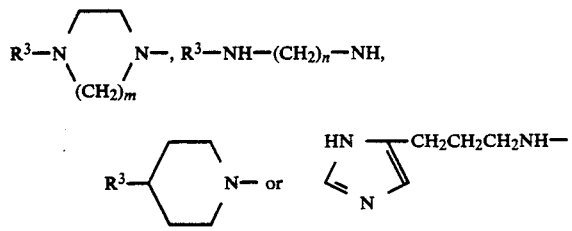

wherein
R$^3$ denotes a hydrogen atom, a C$_1$ to C$_6$ alkyl group optionally substituted with an amino or hydroxyl group, an optionally substituted aryl or heteroaryl group, a cyano group, an acyl group, an optionally substituted aroyl group, a carboxyl group or a C$_1$ to C$_6$ alkoxycarbonyl group, m stands for an integer with a value from 1 to 3 and n stands for an integer with a value from 2 to 4, and the physiologically acceptable salts thereof.

In the general formula I, the group denoted by R$^1$, which is preferably attached in the meta position relating to the pyridazinone ring is a nitro group, an amino group, a hydroxyl group, a cyano group or a halogen atom, for example a fluorine, chlorine or bromine atom, preferably a fluorine or chlorine atom. Compounds in which R$^1$ stands for a nitro or amino group and R$^1$ is attached in the meta position relating to the pyridazinone ring are particularly preferred.

R$^2$ denotes a hydrogen atom, a methyl group or a hydroxymethyl group, preferably a methyl group.

A stands for a group denoted by one of the following formulae.

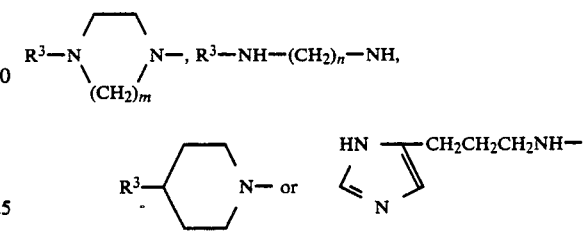

In the groups shown above, R$^3$ stands for a hydrogen atom or for a C$_1$ to C$_6$ alkyl group optionally substituted with an amino or hydroxy group, preferably a C$_1$ to C$_4$ alkyl group. The C$_1$ to C$_6$ alkyl group may be, for example, the methyl, ethyl, n-propyl, isopropyl and n-butyl group. When the C$_1$ to C$_6$ alkyl group is substituted, the substituent is preferably in the end position.

R$^3$ may also stand for an aryl or heteroaryl group which may be substituted with one or two halogen atoms, for example with fluorine, chlorine or bromine atoms, or with one or two C$_1$ to C$_3$ alkyl groups such as methyl, ethyl or propyl groups or with one or two C$_1$ to C$_3$ alkoxy groups such as methoxy or ethoxy groups. Examples of aryl groups include the phenyl group and the naphthyl group, the phenyl group being preferred. Examples of heteroaryl groups include the furanyl, thiophenyl, imidazolyl, pyridyl and pyrimidinyl group, the imidazolyl, pyridyl and pyrimidinyl group being preferred.

R$^3$ may also stand for a cyano group, a C$_1$ to C$_6$ acyl group, for example a formyl, acetyl or propionyl group, an aroyl group, for example a benzoyl group which is optionally substituted with one or more, for example two, halogen atoms or with C$_1$ to C$_3$ alkyl groups or C$_1$ to C$_3$ alkoxy groups. Specific examples of the substituents on the aroyl groups are the special groups and atoms mentioned above as substituents on the aryl or heteroaryl group.

Lastly, R$^3$ may denote a carboxyl group or a C$_1$ to C$_6$ alkoxycarbonyl group, for example a methoxycarbonyl, ethoxycarbonyl or tert.-butoxycarbonyl group, the ethoxycarbonyl group being preferred. The number denoted by m is in all cases an integer with a value from 1 to 3, preferably 2 while n has the value 2, 3 or 4, preferably 2 or 3.

A preferred group of compounds according to the present invention is characterised in that R$^1$ in the general formula I stands for a nitro group, an amino group, a hydroxy group, a cyano group or a halogen atom, in particular a nitro or amino group, R$^2$ stands for a hydrogen atom, a methyl group or a hydroxymethyl group, the methyl group being preferred, and A stands for a group of the formula

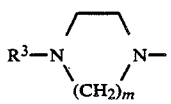

wherein $R^3$ denotes a hydrogen atom, a $C_1$ to $C_6$ alkyl group optionally substituted with an amino or hydroxyl group, in particular a 2-aminoethyl or 3-aminopropyl group, an optionally substituted aryl or heteroaryl group, a cyano group, an acyl group, an optionally substituted aroyl group or a $C_1$ to $C_6$ alkoxycarbonyl group, in particular a methoxycarbonyl or ethoxycarbonyl group, and m has a value from 1 to 3, preferably the value 2.

Another preferred group of compounds according to the present invention is characterised in that in the general formula I, $R^1$ stands for a nitro group, an amino group, a hydroxyl group, a cyano group or a halogen atom, $R^2$ denotes a hydrogen atom or a methyl group, A stands for a group of the formula $R^3$—NH—$(CH_2)_n$—NH wherein $R^3$ denotes a hydrogen atom, an optionally substituted aryl or heteroaryl group, an acyl group, an optionally substituted aroyl group or a $C_1$ to $C_6$ alkoxycarbonyl group, and n has a value from 2 to 4, preferably the value 2 or 3.

Yet another preferred group of compounds according to the invention is characterised in that in the general formula I, $R^1$ stands for a nitro group, an amino group, a hydroxyl group, a cyano group or a halogen atom, $R^2$ denotes a hydrogen atom or a methyl group and A stands for a group of the formula

wherein $R^3$ stands for a $C_1$ to $C_6$ alkyl group optionally substituted with an amino or hydroxyl group, an optionally substituted aryl or heteroaryl group, an acyl group, an optionally substituted aroyl group, a carboxyl group or a $C_1$ to $C_6$ alkoxycarbonyl group.

Lastly, another preferred group of compounds according to the present invention is characterised in that $R^1$ stands for a nitro group, an amino group, a hydroxyl group, a cyano group or a halogen atom, $R^2$ stands for a hydrogen atom, a methyl group or a hydroxymethyl group and A stands for the group corresponding to the formula

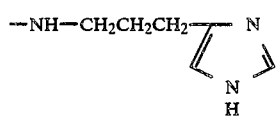

The following are specific compounds which are preferred:
6-[3-nitro-4-(1-piperazinyl)-phenyl]-4,5-dihydro-5-methyl-3(2H)-pyridazinone;
6-[4-(4-ethoxycarbonylpiperazin-1-yl)-3-nitrophenyl]-4,5-dihydro-5-methyl-3-(2H)-pyridazinone;
6-[3-amino-4-(4-ethoxycarbonylpiperazin-1-yl)-phenyl]-4,5-dihydro-5-methyl-3(2H)-pyridazinone;
6-[4-(4-acetylpiperazin-1-yl)-3-nitrophenyl]-4,5-dihydro-5-methyl-3(2H)-pyridazinone;
6-[4-(4-ethoxycarbonylpiperazin-1-yl)-3-nitrophenyl]-4,5-dihydro-3-(2H)-pyridazinone;
and their physiologically acceptable salts.

The compounds according to the invention may be prepared by various processes.

One process which is suitable in general for the preparation of the compounds according to the invention, i.e. compounds corresponding to the general formula I in which A, $R^1$ and $R^2$ have the meanings defined above, is characterised in that a compound corresponding to the general formula II

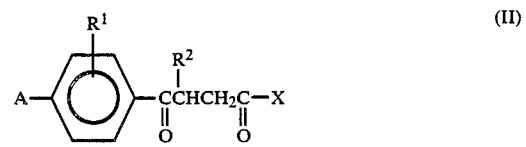

in which A, $R^1$ and $R^2$ have the meanings defined above and X stands for the group OH or a group of the formula $OR^4$ in which $R^4$ denotes an optionally substituted $C_1$ to $C_6$ alkyl group or an optionally substituted aryl group, is reacted with hydrazine or a chemical equivalent thereof to form a compound corresponding to the general formula I and the resulting compound is optionally converted into a physiologically acceptable salt thereof in known manner.

The term "chemical equivalents of hydrazine" is understood to mean hydrazine hydrate, hydrazine ethanolate and similar solvates or salts thereof. The reactions with hydrazine or a chemical equivalent thereof are preferably carried out with an excess of reactant in a polar solvent, for example acetic acid or an alcohol such as methanol, ethanol or isopropanol. The reaction is carried out at temperatures from room temperature to the reflux temperature of the solvent used, preferably the reflux temperature.

Compounds corresponding to the general formula I in which A and $R^2$ have the meanings defined above and $R^1$ stands for a nitro group may also be prepared by reacting a compound corresponding to the general formula III

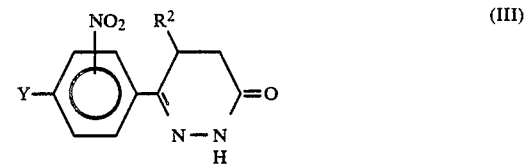

wherein $R^2$ has the meaning defined above and Y stands for a halogen atom, for example a fluorine, chlorine or bromine atom, with a compound corresponding to the general formula IV $$H—A \qquad (IV)$$

in which A has the meaning defined above. For this reaction, the compound of formula IV is preferably used in excess, in particular in a two to three times molar quantity, based on the compound of the general formula III. The reactions are carried out in an inert solvent such as dimethyl formamide, dimethyl sulphoxide, acetonitrile, dioxane or tetrahydrofuran at an elevated temperature, preferably in the range of from 80° to 180° C. The acid H—X formed in the reaction is absorbed either by the excess of the compound of the general formula IV or by an auxiliary base added to the reaction mixture, such as potassium carbonate, triethylamine or pyridine.

Compounds corresponding to the general formula I in which A and $R^2$ have the meanings defined above and $R^1$ stands for an amino group may also be prepared by reducing a compound of the general formula Ia

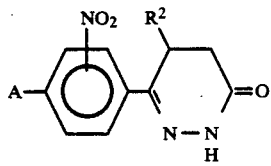
(Ia)

in which A and $R^2$ have the meanings defined above and $R^1$ is a nitro group by means of a suitable reducing agent. The reducing agents used for reduction of the nitro group to the amino group may be, for example, base metals or their salts in an acid medium, such as iron in hydrochloric acid, tin or tin dichloride in hydrochloric acid or zinc in acetic acid; sulphur compounds such as ammonium sulphide, sodium sulphide or sodium dithionite; hydrazine or a chemical equivalent thereof in the presence of a catalyst such as Raney nickel; cyclohexene in the presence of a noble metal catalyst such as platinum oxide or palladium; or hydrogen in the presence of catalysts such as Raney nickel, palladium or platinum oxide.

Compounds corresponding to the general formula I in which A and $R^2$ have the meanings indicated above and $R^1$ stands for a hydroxyl group, a cyano group or a halogen atom may also be prepared by diazotizing a compound corresponding to the general formula Ib

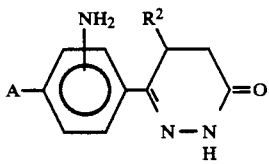
(Ib)

wherein A and $R^2$ have the meanings defined above to a compound corresponding to the general formula V

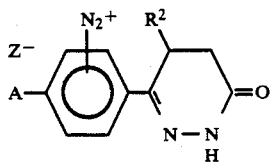
(V)

wherein A and $R^2$ have the meanings defined above and Z stands for a halogen atom, a hydroxyl group, a cyano group or the tetrafluoroborate group, and decomposing the diazonium salt corresponding to the general formula V by heat, optionally in the presence of copper powder or a copper-(I) halide or copper-(I) cyanide. Diazotization of the aromatic amine of formula Ib, for example, may be carried out with an alkali metal nitrite such as sodium nitrite in an acid aqueous solution at a temperature from −10° C. to 10° C., preferably at 0° to 5° C.

Decomposition of the diazonium salt by heat takes place at temperatures from 30° to 150° C., the diazonium group on the aromatic ring being replaced by a hydroxyl group, a cyano group or a halogen atom. When the halogen atom is a chlorine, bromine or iodine atom, it is advantageous to add copper powder or the corresponding copper-(I) halide. When $R^1$ introduced is fluorine then $Z^-$ is a fluoride or tetrafluoroborate anion. When a cyano group is introduced, the diazonium salt corresponding to formula V may be reacted, for example, with copper-(I) cyanide dissolved as a complex in potassium cyanide.

Compounds corresponding to the general formula I in which $R^1$ and $R^2$ have the meanings defined above and A stands for a group of the formula

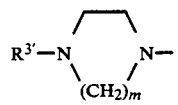

or a group of the formula $R^{3'}$—NH—$(CH_2)_n$—NH in which m and n have the meanings defined above and $R^{3'}$ stands for a cyano group, an acyl group, an optionally substituted aroyl group or a $C_1$ to $C_6$ alkoxycarbonyl group may also be prepared by the reaction of a compound corresponding to the general formula Ic or Id

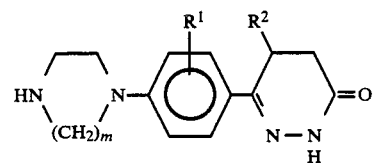
(Ic)

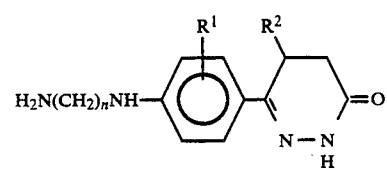
(Id)

in which $R^1$, $R^2$, m and n have the meanings indicated above with an acylating agent corresponding to the general formula VI $R^{3'}$—L  (VI)

wherein $R^{3'}$ has the meaning indicated above and L stands for a halogen atom, in particular a chlorine or bromine atom, the group $OR^{3'}$, the hydroxyl group or an azole or benzazole group which has at least two nitrogen atoms in the 5 membered ring and is attached by a nitrogen atom. Examples of the above mentioned azoles or benzazoles include the imidazole, the 1,2,4-triazole, the tetrazole, the benzimidazole or the benzotriazole ring. When the acylating agent used is a compound corresponding to the general formula VI in which L stands for the group OH then it is advisable to add an activating agent to increase the acylating potential of the carboxylic acid. Suitable agents of this type include dehydrating and water binding agents, for example carbodiimides, or agents which convert the carboxylic acids into the corresponding acid halides, anhydrides, mixed carboxyliccarbonic acid anhydrides or azolides, which then function as acylating agents. Examples of the latter type of agent include phosgene, chloroformic acid esters and N,N'-carbonyldiimidazole. The reaction between the acylating agent of the general formula VI and compounds of the general formulae Ic and Id is preferably carried out in an inert solvent, e.g. a halogenated hydrocarbon, an ether or a solvent such as pyridine or dimethyl formamide at temperatures from −20° C. to the boiling point of the solvent. The molar ratio of acylating agent of formula VI to compounds of the general formulae Ic and Id is normally in the range of 3:1 to 1:1, preferably from 2:1 to 1:1. If an acid is split off in the acylating reaction, it is advisable to add an acid acceptor, for example a tertiary amine such as triethylamine or pyridine.

Compounds corresponding to the general formula I in which $R^1$ and $R^2$ have the meanings defined above and A stands for a group of the formula

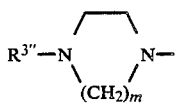

or a group of the formula $R^{3''}$—NH—$(CH_2)_n$—NH wherein m and n have the meanings defined above and $R^{3''}$ stands for a hydrogen atom may be prepared by acid or basic hydrolysis and optionally decarboxylation of a compound corresponding to the general formula I in which $R^1$ and $R^2$ have the meanings defined above and A stands for a group of the formula

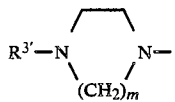

or $R^{3'}$—NH—$(CH_2)_n$—NH in which $R^{3'}$ stands for a cyano group, an acyl group, an optionally substituted aroyl group or a $C_1$ to $C_6$ alkoxycarbonyl group.

The acid hydrolysis may be carried out, for example, in aqueous mineral acids such as hydrochloric or hydrobromic acid or sulphuric acid and at elevated temperatures. In special cases, for example when $R^{3'}$=tert.-butoxycarbonyl, milder methods may be employed, such as hydrolysis with trifluoro-acetic acid in a chlorinated hydrocarbon such as dichloromethane or chloroform.

Basic hydrolysis is carried out in dilute solutions of alkali metal or alkaline earth metal carbonates or alkali metal or alkaline earth metal hydroxides in water, lower alcohols or mixtures of the two and at temperatures from room temperature to the reflux temperature of the solvent used.

The compounds obtained by the different variations of the process are isolated and purified in the usual manner, for example by recrystallization, chromatographic procedures, etc.

The compounds obtained from the different variations of the process may optionally be converted into physiologically acceptable salts thereof. These salts may be formed, for example, with mineral acids such as hydrochloric, hydrobromic or hydriodic acid, phosphoric acid, metaphosphoric acid, nitric or sulphuric acid or with organic acids such as formic acid, acetic acid, propionic acid, phenyl acetic acid, tartaric acid, citric acid, fumaric acid, methane sulphonic acid, embonic acid, etc.

The compounds according to the invention corresponding to the general formula I may be present in various tautomeric forms and in several stereo isomeric forms. This invention therefore covers not only the salts and hydrates of the above described compounds corresponding to the general formula I but also all tautomeric and stereo isomeric forms.

The compounds according to the invention may be formulated in any desired manner for administration. This invention therefore also covers pharmaceutical preparations containing at least one compound according to the invention for use in human or veterinary medicine. Such pharmaceutical preparations may be prepared by the conventional methods using one or more pharmaceutically acceptable carriers or diluents.

The compounds according to the invention may therefore be formulated for oral, buccal, topical, parenteral or rectal administration.

For oral administration, the medicament may, for example, be made up into tablets, capsules, powders, solutions, syrups or suspensions by the usual methods using acceptable diluents.

For buccal administration, the pharmaceutical preparation may be in the form of tablets or sachets formulated in the conventional manner.

The compounds according to the invention may be formulated for parenteral administration by bolus injection or continuous infusion. Formulations for injection may be provided in the form of ampoules containing unit doses or multiple dose containers with added preservative.

The pharmaceutical preparations may assume forms such as suspensions, solutions or emulsions in oily or aqueous carriers and may contain formulating auxiliaries such as suspending, stabilizing and/or dispersing agents.

Alternatively, the active ingredient may be in the form of a powder to be reconstituted before use with a suitable carrier, for example sterile, pyrogen free water.

The compounds according to the invention may also be formulated for rectal preparations such as suppositories or retention enemas containing, for example, the usual excipients for suppositories, such as cocoa butter or other glycerides.

For topical use, the compounds according to the invention may be formulated as ointments, creams, gels, lotions, powders or sprays in the usual manner.

For oral administration, a suitable daily dose of compounds according to the invention is taken in 1 to 4 doses with a total of 5 mg to 1 g per day, depending on the patient's condition. It may in some cases be necessary to deviate from the quantities indicated above, depending on the individual's response to the active ingredient, the nature of the formulation, and the time or interval of time at which the preparation is administered. Thus there are cases, for example, in which it may be sufficient to use less than the minimum quantity indicated above whereas in other cases it may be necessary to exceed the upper limit.

The substituted 6-phenyl-dihydro-3(2H)-pyridazinones according to the invention corresponding to the general formula I are not only easily available for oral administration but have pronounced cardiovascular, in particular cardiotonic and antihypertensive actions and are therefore suitable for the treatment and prevention of diseases of the heart and circulation.

Thus they have an excellent positive inotropic effect in various pharmacological standard models, e.g. an in vivo model of narcotised guinea pig after i.d. application, and lower the blood pressure in spontaneously hypertensive rats.

1. Haemodynamic characterisation of the positive inotropic action on narcotised guinea pigs (i.d. application)

(a) Method

The animals are narcotised with urethane (1.5 g/kg). The trachea is cannulated for volume-controlled respiration. The two carotid arteries are then exposed operatively and a Tip catheter (3F) is introduced through the right carotid and moved forwards through the ascending aorta into the left ventricle with continuous recording of the pressure. Successful passage through the aortic valves is indicated by the typical left ventricular pressure curve. A thermistor probe (RF, F. Edwards) is pushed forwards into the aortic arch through the left carotid for thermodilution. The thermistor probe has a lumen for recording the arterial blood pressure. A catheter is passed through the right jugular vein to be placed in front of the right auricle for application of the cold injectate (0.2 ml 0.9% NaCl, 15° C.). The ECG is recorded in the first lead. The duodenum is exposed by a median section 1 cm in length in the upper abdominal region; the test substances are injected into the duodenum through a needle. All substances are suspended in tylose (injection volume 1 ml/kg) and applied after haemodynamic stabilization and under β-blockage (Metoprolol 2 mg/kg i.m.). All circulation parameters are continuously recorded on a direct recorder. The contractility (dp/dt) is calculated from the volume pressure curve and the cardiac frequency is determined from the ECG.

(b) Measured Values

| Example No. | Dose mg/kg | Maximum Percentage Changes from Initial Values | | |
|---|---|---|---|---|
| | | Contractility dp/dt | Blood Pressure Systolic | Cardiac Frequency |
| 2 | 0.2 | +70% | −20% | +13% |
| 3 | 3.1 | +40% | −20% | +10% |
| 6 | 12.5 | +67% | −21% | +7% |
| 12 | 10 | +70% | −25% | +25% |
| Comparison 1* | 50 | +22% | −44% | +22% |
| Comparison 2** | 50 | +58% | −40% | +48% |

*Comparison 1:
6-(4-morpholino-3-nitro-phenyl)-4,5-dihydro-5-methyl-3(2H)-pyridazinone.
**Comparison 2:
6-[4-(4-ethoxycarbonyl-piperazin-1-yl)-phenyl]-4,5-dihydro-3(2H)-pyridazinone (DE-OS 22 07 517).

Antihypertensive action on spontaneously hypertensive rats

The method described in the literature by I. B. Armah, Arzneimittelforsch 27, 1882–1884 (1977) and M. Gerold and H. Tschirky, Arzneimittelforsch 18, 1285 (1968) was employed. The substances were administered orally and the lowering of blood pressure was determined three hours after application of the substance.

| Example No. | Dose mg/kg | Lowering of Blood Pressure After 3 Hours |
|---|---|---|
| 2 | 5 | 82% |
| Comparison 1 | 5 | 17% |
| Comparison 2 | 5 | 29% |

EXAMPLE 1

6-[3-nitro-4-(1-piperazinyl)-phenyl]-4,5-dihydro-5-methyl-3(2H)-pyridazinone

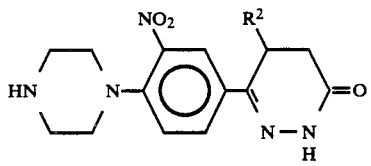

21.4 g (80 mmol) of 6-(4-chloro-3-nitro-phenyl)-4,5-dihydro-5-methyl-3(2H)-pyridazinone are boiled under reflux together with 41.35 g (480 mmol) of piperazine in 120 ml of dioxane for 5 hours.

After cooling, the reaction mixture is poured out on 400 ml of water, stirred for 1 hour to complete crystallization, suction filtered and washed with water.

Recrystallization from methoxyethanol/diethyl ether yields 19.4 g (76% of theoretical) of an orange red powder, melting point 224° to 225° C.

$C_{15}H_{19}N_5O_3$ (317.35)

Rf=0.40 (dichloromethane/methanol/triethylamine 90/7/3)

EXAMPLE 2

6-[4-(4-ethoxycarbonyl-piperazin-1-yl)-3-nitro-phenyl]-4,5-dihydro-5-methyl-3(2H)-pyridazinone

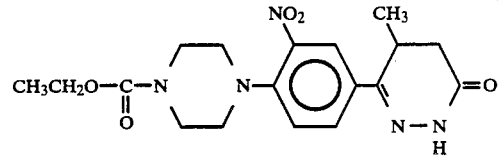

24.5 ml (168 mmol) of 1-ethoxycarbonylpiperazine are added to a solution of 15.0 g (56 mmol) of 6-(4-chloro-3-nitro-phenyl)-4,5-dihydro-5-methyl-3(2H)-pyridazinone in 50 ml of dimethyl formamide and the solution is stirred at a reaction temperature of 100° C. for 3 hours. When the reaction mixture is cold, it is poured out on 300 ml of ice water with vigorous stirring. The precipitated solid is suction filtered, washed with a small quantity of ethanol and diethyl ether and recrystallized from 500 ml of ethanol. 16.7 g (76%) of orange yellow crystals, m.p. 140° to 142° C., are obtained.

$C_{18}H_{23}N_5O_5$ (389.41)

Rf=0.50 (dichloromethane/methanol 95/5)

EXAMPLE 3

6-[4-(4-ethoxycarbonyl-piperazin-1-yl)-3-nitro-phenyl]-4,5-dihydro-3(2H)-pyridazinone

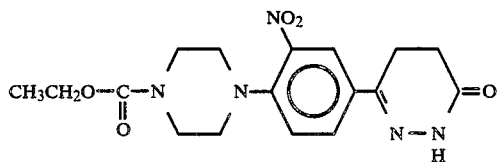

10.14 g (90%) of orange yellow crystals melting at 203° to 204° C. are obtained by a method analogous to that of Example 2 from 7.61 g (30 mmol) of 6-(4-chloro-3-nitro-phenyl)-4,5-dihydro-3(2H)-pyridazinone and 14.25 g (90 mmol) of 1-ethoxycarbonyl-piperazine.

$C_{17}H_{21}N_5O_5$ (375.39)

Rf=0.18 (dichloromethane/methanol 97/3)

EXAMPLE 4

6-[4-(4-benzyl-piperazin-1-yl)-3-nitro-phenyl]-4,5-dihydro-5-methyl-3(2H)-pyridazinone

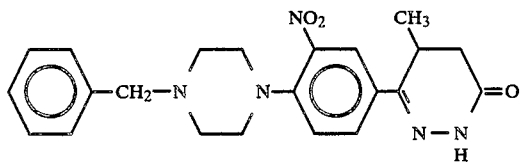

16.1 g (60 mmol) of 6-(4-chloro-3-nitro-phenyl)-4,5-dihydro-5-methyl-3(2H)-pyridazinone, 15.9 g (90 mmol) of 1-benzyl-piperazine and 7.3 ml (90 mmol) of pyridine are stirred into 60 ml of dimethyl formamide at 100° C. A further 5.8 g (33 mmol) of 1-benzyl-piperazine is added after 7 hours and stirring of the reaction mixture is continued for 12 hours at 100° C. When the reaction mixture is cold it is poured out on 300 ml of ice water and the solid which precipitates is suction filtered. The aqueous phase is extracted twice with 200 ml of dichloromethane. The combined organic phases are washed with water and saturated sodium chloride solution, dried, filtered and concentrated by evaporation in vacuo. The solid residue obtained is recrystallized from 500 ml of ethanol together with the solid initially obtained. 23.4 g (95%) of orange red crystals melting at 220° to 221° C. are obtained.

$C_{22}H_{25}N_5O_3$ (407.48)

Rf=0.50 (dichloromethane/methanol 95/5)

EXAMPLE 5

6-[3-nitro-4-[4-(2-pyrimidyl)-piperazin-1-yl]phenyl]-4,5-dihydro-5-methyl-3(2H)-pyridazinone

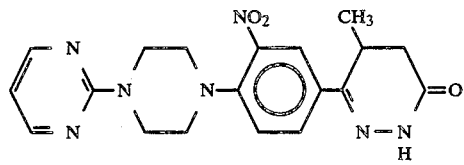

3.0 g (11.2 mmol) of 6-(4-chloro-3-nitro-phenyl)-4,5-dihydro-5-methyl-3(2H)-pyridazinone, 3.7 g (22.4 mmol) of 1-(2-pyrimidyl)-piperazine and 0.9 g (11.2 mmol) of pyridine are boiled under reflux in 50 ml of dioxane. A further 1.9 g (11.6 mmol) of 1-(2-pyrimidyl)-piperazine is added after 6 hours and the reaction mixture is boiled for a further 4 hours. When the reaction mixture has cooled, it is poured out on 300 ml of ice water and the precipitated solid is suction filtered, washed with a small quantity of diethyl ether and recrystallized from 40 ml of 2-methoxyethanol. 3.1 g (70%) of orange red crystals, m.p. 232° to 233° C., are obtained.

$C_{19}H_{21}N_7O_3$ (395.42)

Rf=0.60 (dichloromethane/methanol 95/5)

EXAMPLE 6

6-[4-(4-acetyl-piperazin-1-yl)-3-nitro-phenyl]-5-methyl-4,5-dihydro-3(2H)-pyridazinone

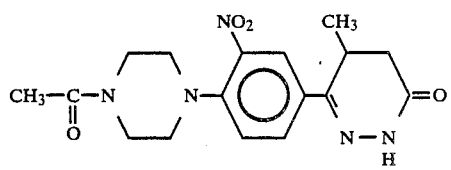

(a) 0.57 ml (6 mmol) of acetic acid anhydride are added at room temperature to 1.27 g (4 mmol) of 6-[3-nitro-4-(1-piperazinyl)-phenyl]-4,5-dihydro-5-methyl-3(2H)-pyridazinone in 30 ml of acetic acid.

The reaction mixture is heated to 60° C. for 10 minutes, left to cool, poured out on ice water and extracted with chloroform. The chloroform phase is washed with aqueous $NaHCO_3$ solution and concentrated by evaporation in vacuo. The solid residue is recrystallized from 20 ml of methoxyethanol. 0.8 g (56% of theoretical) of the title compound is obtained as an orange coloured powder, m.p. 240° to 241° C.

$C_{17}H_{21}N_5O_4$ (359.31)

Rf=0.55 (dichloromethane/methanol 95/5)

(b) 2.68 g (10 mmol) of 6-(4-chloro-3-nitro-phenyl)-4,5-dihydro-5-methyl-3(2H)-pyridazinone and 3.84 g (30 mmol) of 1-acetylpiperazine are stirred together in 20 ml of dimethyl formamide at a reaction temperature of 100° C. for 4 hours. When the reaction mixture has cooled, it is poured out on 200 ml of ice water and the resulting solid is suction filtered and recrystallized from methoxyethanol. 2.30 g (64%) of orange coloured crystals melting at 240° to 241° C. and identical to the product described under (a) are obtained.

EXAMPLE 7

6-[4-(4-formyl-piperazin-1-yl)-3-nitro-phenyl]-4,5-dihydro-5-methyl-3(2H)-pyridazinone

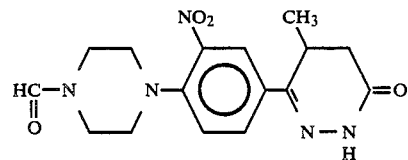

2.35 g (68%) of orange red crystals melting at 216.5° C. are obtained (from chloroform/methanol 1:3) by a method analogous to that of Example 6b) from 2.68 g (10 mmol) of 6-(4-chloro-3-nitro-phenyl)-4,5-dihydro-5-methyl-3(2H)-pyridazinone and 3.42 g (30 mmol) of 1-formylpiperazine.

$C_{16}H_{19}N_5O_4$ (345.36)

Calculated: C 55.65; H 5.55; N 20.28. Found: C 55.70; H 5.56; N 20.25.

Rf=0.62 (dichloromethane/methanol/conc. ammonia 90/7/3)

EXAMPLE 8

6-[4-[4-(4-methoxybenzoyl)-piperazin-1-yl]-3-nitro-phenyl]-5-methyl-4,5-dihydro-3(2H)-pyridazinone

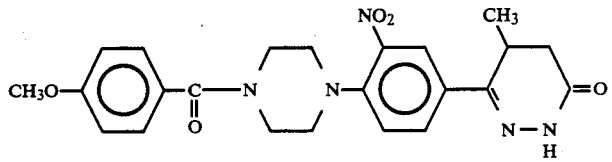

0.70 g (4.1 mmol) of 4-methoxybenzoyl chloride is added to a slurry of 1.0 g (3.15 mmol) of 6-[3-nitro-4-(1-piperazinyl)-phenyl]-5-methyl-4,5-dihydro-3(2H)-pyridazinone and 1.14 ml (8.2 mmol) of triethylamine in 40 ml of 1,2-dichloroethane and the reaction mixture is boiled under reflux for 0.5 h. It is then cooled to room temperature, 50 ml of water are added, and the organic phase is separated off.

After concentration of the organic phase by evaporation, the residue is chromatographed on silica gel (solvent: dichloromethane/methanol 97/3). 0.69 g (49% of theoretical) of the title compound is obtained as orange yellow crystals, melting point 200° to 201° C.

$C_{23}H_{25}N_5O_5$ (451.48)
Rf=0.44 (dichloromethane/methanol 95/5)

EXAMPLE 9

6-[4-(4-cyano-piperazin-1-yl)-3-nitro-phenyl]-5-methyl-4,5-dihydro-3(2H)-pyridazinone

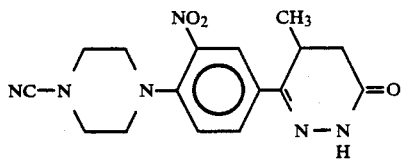

1.58 g (5 mmol) of 6-[3-nitro-4-(1-piperazinyl)-phenyl]-5-methyl-4,5-dihydro-3(2H)-pyridazinone is made up into a slurry with 60 ml of chloroform, and a solution of 0.64 g (6 mmol) of cyanogen bromide in 10 ml of chloroform is added dropwise at 10° C.

After 0.5 h., 40 ml of water are added to the reaction mixture, followed by a solution of 2 g of potassium carbonate in 5 ml of water. Stirring is then continued for 1 hour while the title compound crystallizes.

The solid is removed by suction filtration, washed with water and acetone and recrystallized from acetone/1,2-dichloroethane.

0.96 g (56% of theoretical) of orange red crystals, melting point 247°-248° C., are obtained.

$C_{16}H_{18}N_6O_3$ (342.36)
Rf=0.45 (dichloromethane/methanol 97/3)

EXAMPLE 10

6-[4-(2-tert.-butoxycarbonylamino)ethylamino-3-nitro-phenyl]-4,5-dihydro-5-methyl-3(2H)-pyridazinone

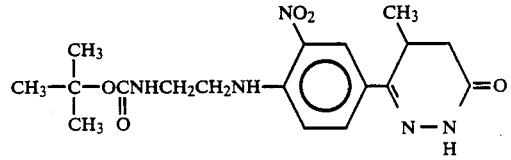

2.68 g (10 mmol) of 6-(4-chloro-3-nitro-phenyl)-4,5-dihydro-5-methyl-3(2H)-pyridazinone and 4.80 g (30 mmol) of N-tert.-butoxycarbonyl-ethylene diamine are stirred in 20 ml of dimethyl formamide for 3.5 hours at 80° C. When the reaction mixture is cold, it is poured into 150 ml of water and the solid which precipitates is separated by suction filtration. After recrystallization from dichloromethane, 1.70 g (43%) of orange red crystals, m.p. 225°-226° C. are obtained.

$C_{18}H_{25}N_5O_5$ (391.43)
Rf=0.68 (dichloromethane/methanol 9/1)

EXAMPLE 11

6-[4-(3-tert.-butoxycarbonylamino)propylamino-3-nitro-phenyl]-4,5-dihydro-5-methyl-3(2H)-pyridazinone

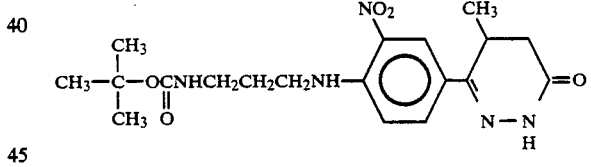

2.68 g (10 mmol) of 6-(4-chloro-3-nitro-phenyl)-4,5-dihydro-5-methyl-3(2H)-pyridazinone and 5.22 g (30 mmol) of N-tert.-butoxycarbonyl-1,3-propane diamine are treated by a method analogous to that of Example 10 to yield 0.92 g (23%) of an orange red solid, m.p. 172°-173° C., after chromatographic purification on silica gel with dichloromethane/methanol (90:10) as solvent and recrystallization from dichloromethane.

$C_{19}H_{27}N_5O_5$ (405.46)
Rf=0.65 (dichloromethane/methanol 9/1)

EXAMPLE 12

6-[3-amino-4-(4-ethoxycarbonyl-piperazin-1-yl)-phenyl]-4,5-dihydro-5-methyl-3(2H)-pyridazinone

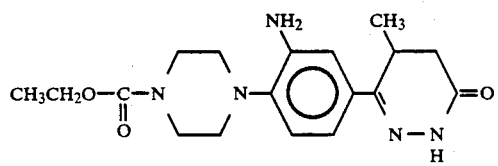

13.7 g (35 mmol) of 6-[4-(ethoxycarbonyl-piperazin-1-yl)-3-nitro-phenyl]-4,5-dihydro-5-methyl-3(2H)-pyridazinone in 500 ml of methanol are hydrogenated for 1 hour under a hydrogen pressure of 6 bar at 55° C. in the presence of 1.0 g of palladium on active charcoal (10% Pd). After removal of the catalyst by suction filtration, the solution is to a large extent evaporated under vacuum and the residue is stirred up with 50 ml of a mixture of diethyl ether/ethyl acetate (2:1). The precipitated solid is suction filtered and recrystallized from ethanol. 8.6 g (68%) of a pale yellow solid, m.p. 193°–195° C., are obtained.

$C_{18}H_{25}N_5O_3$ (359.43)

Rf=0.45 (dichloromethane/methanol 95/5)

EXAMPLE 13

6-[4-(2-aminoethyl)amino-3-nitro-phenyl]-4,5-dihydro-5-methyl-3(2H)-pyridazinone

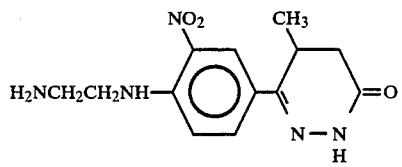

1.0 ml (13.0 mmol) of trifluoroacetic acid is added to 1.00 g (2.55 mmol) of 6-[4-(2-tert.-butoxycarbonylamino)ethylamino-3-nitro-phenyl]-4,5-dihydro-5-methyl-3(2H)-pyridazinone in 10 ml of dichloromethane and the solution is boiled under reflux for 2 hours. After cooling to room temperature, the reaction mixture is diluted with 10 ml of dichloromethane and the solid which precipitates is filtered off and introduced into 20 ml of saturated sodium bicarbonate solution. The solid which then separates is filtered off and recrystallized from isopropanol. 0.44 g (59%) of an orange red solid, m.p. 162°–164° C., is obtained.

$C_{13}H_{17}N_5O_3$ (291.31)

Rf=0.65 (ethyl acetate/ethanol/conc. ammonia 15/10/2).

EXAMPLE 14

6-[4-(3-aminopropyl)amino-3-nitro-phenyl]-4,5-dihydro-5-methyl-3(2H)-pyridazinone

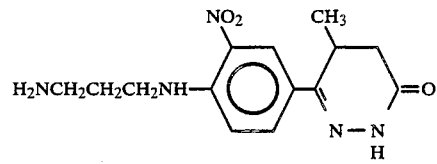

2.0 g (4.9 mmol) of 6-[4-(3-tert.-butoxycarbonylamino)propylamino-3-nitro-phenyl]-4,5-dihydro-5-methyl-3(2H)-pyridazinone and 2.0 ml (26.1 mmol) of trifluoro-acetic acid are boiled under reflux in 30 ml of chloroform for 12 hours. The oil obtained after removal of the solvent by evaporation under vacuum is taken up with 10 ml of a saturated potassium carbonate solution and the aqueous phase is extracted three times with 20 ml portions of isopropanol. The combined organic phases are dehydrated with sodium sulphate, filtered and concentrated by evaporation under vacuum. The residue is chromatographed on silica gel with dichloromethane/methanol (9:1) as solvent. After concentration of the main fraction by evaporation under vacuum and recrystallization from isopropanol, 1.0 g (66%) of an orange red solid, m.p. 154°–156° C., is obtained.

$C_{14}H_{19}N_5O_3$ (305.33)

Rf=0.46 (ethyl acetate/ethanol/conc. ammonia 15/10/2)

EXAMPLE 15

6-[4-(4-ethoxycarbonyl-piperidin-1-yl)-3-nitro-phenyl]-5-methyl-4,5-dihydro-3(2H)-pyridazinone

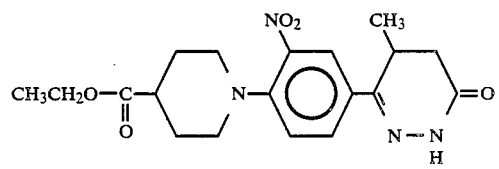

2.68 g (10 mmol) of 6-(4-chloro-3-nitro-phenyl)-5-methyl-4,5-dihydro-3(2H)-pyridazinone are boiled under reflux with 3.14 g (20 mmol) of piperidine-4-carboxylic acid ethyl ester and 0.81 ml (10 mmol) of pyridine in 50 ml of dioxane for 5 hours. The reaction mixture is then poured out on 200 ml of ice water and suction filtered to separate the solid, and the filter cake is then washed with water.

After recrystallization from 100 ml of ethanol, 2.8 g (72% of theoretical) of the title compound are obtained as orange coloured needles, m.p. 159.5°–160.5° C.

$C_{19}H_{24}N_4O_5$

Rf=0.45 (dichloromethane/methanol 97/3)

EXAMPLE 16

6-[3-amino-4-(2-tert.-butoxycarbonylamino)ethylaminophenyl]-4,5-dihydro-5-methyl-3(2H)-pyridazinone

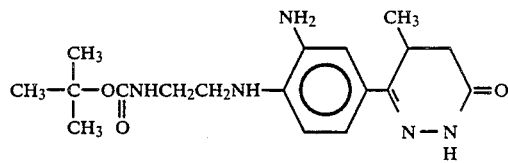

2.5 g (6.4 mmol) of 6-[4-(2-tert.-butoxycarbonylamino)ethylamino-3-nitro-phenyl]-4,5-dihydro-5-methyl-3(2H)-pyridazinone are hydrogenated under a hydrogen pressure of 5 bar at room temperature in the presence of 0.5 g of palladium charcoal (10% Pd). When uptake of hydrogen has been completed, the catalyst is removed by suction filtration and the filtrate is concentrated by evaporation under vacuum. The residue is purified by chromatography on silica gel with dichloromethane/methanol (95:5) as solvent. After concentration by evaporation under vacuum, the main fraction yields 1.6 g (69%) of a greenish, amorphous solid.

$C_{18}H_{27}N_5O_3$ (361.44)

Rf=0.64 (dichloromethane/methanol 9/1)

EXAMPLE 17

1-[4-(5-methyl-3-oxo-2,3,4,5-tetrahydro-6-pyridazinyl)-2-nitro-phenyl]-piperidine-4-carboxylic acid

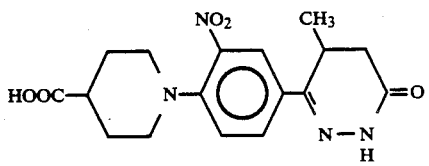

1.2 g (3.1 mmol) of 1-[2-nitro-4-(5-methyl-3-oxo-2,3,4,5-tetrahydro-6-pyridazinyl)-phenyl]-piperidine-4-carboxylic acid ethyl ester are heated under reflux in a solution of 0.4 g (9.3 mmol) of sodium hydroxide in 40 ml of methoxyethanol.

After 2.5 hours, the reaction mixture is poured out on 150 ml of ice water and the aqueous phase is washed with a total of 150 ml of dichloromethane.

The title compound crystallizes after acidification of the aqueous phase to pH 4.5.

Recrystallization from methanol yields 0.6 g (54% of theoretical) of an orange coloured powder having a melting point of 213.6°–214.5° C.

$C_{17}H_{20}N_4O_5$ (360.37)

Rf=0.23 (chloroform/ethanol/acetic acid 96/2/2)

EXAMPLE 18

6-[3-chloro-4-(4-ethoxycarbonylpiperazin-1-yl)phenyl]-4,5-dihydro-5-methyl-3(2H)-pyridazinone

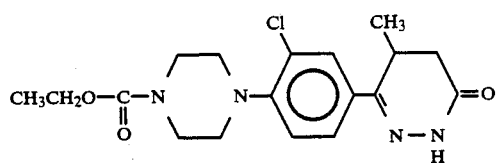

An ice cold solution of 0.9 g (8.5 mmol) of sodium nitrite in 5 ml of water is added dropwise over a period of 10 minutes to a solution of 3.0 g (8.3 mmol) of 6-[3-amino-4-(4-ethoxycarbonylpiperazin-1-yl)-phenyl]-4,5-dihydro-5-methyl-3(2H)-pyridazinone in 7 ml of conc. hydrochloric acid and 3 ml of water at −5° C. The resulting reaction mixture is then added to a solution of 1.29 g (13 mmol) of copper-(I) chloride in 5 ml of conc. hydrochloric acid which is at 0° C. When evolution of gas has ceased, the solution is slowly heated to 50° C. and then cooled and adjusted to pH 11 with potassium carbonate. The aqueous phase is extracted three times with 50 ml of dichloromethane and the organic phases are dried, filtered and concentrated by evaporation under vacuum. The residue obtained is chromatographed on silica gel with dichloromethane/methanol (95:5) and after concentration of the lipophilic main fraction under vacuum it yields 1.2 g (38%) of a colourless solid, m.p. 154°–156° C.

$C_{18}H_{23}ClN_4O_3$ (378.86)

Rf=0.61 (dichloromethane/methanol 95/5)

EXAMPLE 19

6-[4-[3-(4-imidazolyl)-propylamino]-3-nitro-phenyl]-5-methyl-4,5-dihydro-3(2H)-pyridazinone

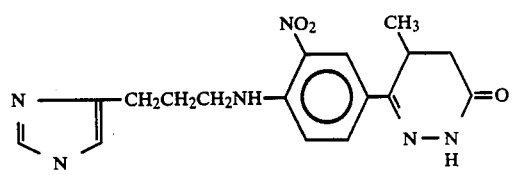

2.67 g (10 mmol) of 6-(4-chloro-3-nitro-phenyl)-5-methyl-4,5-dihydro-3(2H)-pyridazinone are boiled under reflux with 2.5 g (20 mmol) of 4-(3-aminopropyl)-1H-imidazole in 50 ml of dioxane for 5 hours.

The reaction mixture is then poured out on 300 ml of ice water, stirred for 1 hour and suction filtered to separate the precipitated solid.

Recrystallization from acetone yields 2.05 g (58% of theoretical) of orange coloured crystals, melting point 162.7°–163.5° C.

$C_{17}H_{20}N_6O_3$ (356.39)

Rf=0.67 (dichloromethane/methanol/ammonia 85/13/2)

EXAMPLE 20

6-[3-nitro-4-(1-piperazinyl)-phenyl]-4,5-dihydro-3(2H)-pyridazinone

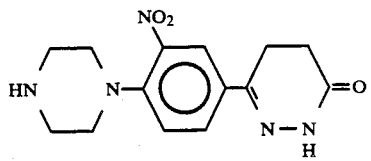

10.0 g (39.4 mmol) of 6-(4-chloro-3-nitro-phenyl)-4,5-dihydro-3(2H)-pyridazinone are boiled under reflux with 10.2 g (118.2 mmol) of piperazine for 5 hours.

After the reaction mixture has cooled to 60° C., it is poured out on ice water and suction filtered to separate the solid and recrystallized from ethanol.

8.8 g (74% of theoretical) of orange red crystals, m.p. 194.7°–196.1° C., are obtained.

$C_{14}H_{17}N_5O_3$ (303.32)

Rf=0.31 (dichloromethane/methanol/triethylamine 90/7/3)

EXAMPLE 21

6-[4-(2-aminoethyl)amino-3-amino-phenyl]-4,5-dihydro-5-methyl-3(2H)-pyridazinone

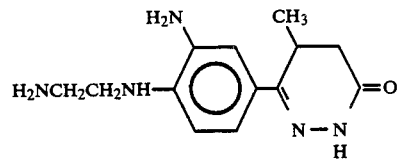

3.0 g (10.3 mmol) of 6-[4-(2-aminoethyl)amino-3-nitro-phenyl]-4,5-dihydro-5-methyl-3(2H)-pyridazinone in 200 ml of methanol are hydrogenated under a hydrogen pressure of 2 bar at room temperature in the presence of 0.5 g of palladium charcoal (10% Pd) until uptake of hydrogen ceases. After removal of the catalyst by filtration, the solution is concentrated by evaporation under vacuum. The residue is chromatographed on silica gel with methanol/conc. ammonia (95/5) as solvent. The main fraction is concentrated by evaporation under vacuum and the solid obtained is recrystallized from ethanol. 1.37 g (51%) of a beige coloured solid, m.p. 176°–177° C. are obtained.

$C_{13}H_{19}N_5O$ (261.32)
Rf=0.34 (methanol/conc. ammonia 95/5)

EXAMPLE 22

6-[3-amino-4-(4-ethoxycarbonyl-piperazin-1-yl)-phenyl]-4,5-dihydro-3(2H)-pyridazinone

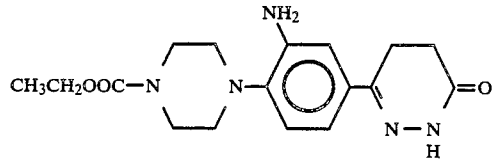

9.0 g (24 mmol) of 6-[4-(4-ethoxycarbonyl-piperazin-1-yl)-3-nitro-phenyl]-4,5-dihydro-3(2H)-pyridazinone are hydrogenated in 150 ml of glacial acetic acid in the presence of 1 g of Pd/active charcoal (10%) at 6 bar and 35° C.

When uptake of hydrogen has ceased, the reaction mixture is filtered and concentrated by evaporation under vacuum and the residue obtained is treated with ethyl acetate and excess aqueous NaHCO₃ solution.

The precipitate is separated by suction filtration and recrystallized from isopropanol to yield 4.35 g (52% of theoretical) of colourless crystals, m.p. 201° C.
$C_{17}H_{23}N_5O_3$ (345.40)
Rf=0.46 (dichloromethane/methanol 95/5)

EXAMPLE 23

6-[3-amino-4-(1-piperazinyl)-phenyl]-5-methyl-4,5-dihydro-3(2H)-pyridazinone

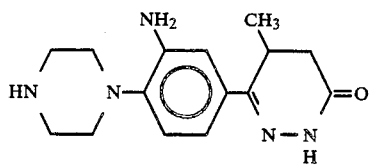

10.0 g (31.5 mmol) of 5-methyl-6-[3-nitro-4-(1-piperazinyl)-phenyl]-4,5-dihydro-3(2H)-pyridazinone are hydrogenated by a method analogous to that of Example 22. Crystallization from isopropanol yields 3.6 g (40% of theoretical) of the title compound melting at 244.4°–244.9° C.

$C_{15}H_{21}N_5O$ (287.37)
Rf=0.24 (dichloromethane/methanol/triethylamine 90/7/3)

EXAMPLE 24

6-[4-[4-(3-aminopropyl)-piperazin-1-yl]-3-nitro-phenyl]-5-methyl-4,5-dihydro-3(2H)-pyridazinone (a)

5-methyl-6-[3-nitro-4-[4-(3-phthalimidopropyl)-piperazin-1-yl]-phenyl]-4,5-dihydro-3(2H)-pyridazinone

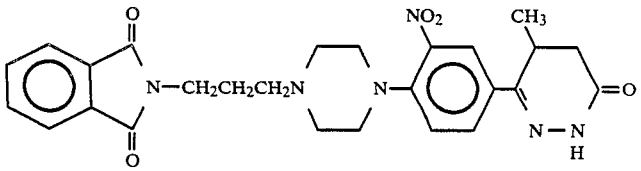

A mixture of 3.16 g (10 mmol) of 5-methyl-6-[3-nitro-4-(1-piperazinyl)-phenyl]-4,5-dihydro-3(2H)-pyridazinone, 2.68 g (10 mmol) of N-(3-bromopropyl)-phthalimide, 1.38 g (10 mmol) of potassium carbonate and 50 ml of dimethyl formamide is stirred at 100° C. for 24 hours.

The reaction mixture is then poured out on 200 ml of ice water, stirred for 1 hour and suction filtered to separate the precipitated solid.

Recrystallization from 300 ml of ethanol yields 3.2 g (64% of theoretical) of an orange red powder, melting point 179.4°–179.9° C.
$C_{26}H_{28}N_6O_5$ (504.55)
Rf=0.28 (dichloromethane/methanol 95/5)

(b)

6-[4-[4-(3-aminopropyl)-piperazin-1-yl]-3-nitro-phenyl]-5-methyl-4,5-dihydro-3(2H)-pyridazinone

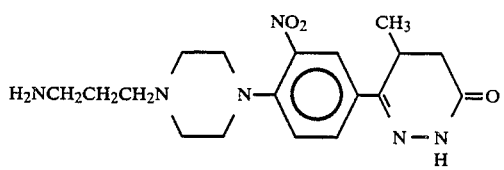

40.4 g (80 mmol) of the above compound are boiled under reflux with 30 ml of hydrazine hydrate (80% in water) in 700 ml of ethanol for 5 hours. Most of the ethanol is distilled off under vacuum. 200 ml of water are added to the residue which is then acidified to pH 2 with dilute hydrochloric acid.

The precipitated solid is removed by suction filtration and the filtrate is adjusted to pH 14 by the addition of sodium hydroxide and stirred in an ice bath until crystallization is complete.

The crystallizate is recrystallized twice from isopropanol. 16.2 g (54% of theoretical) of an orange coloured powder, m.p. 110°–110.5° C., are obtained.
$C_{18}H_{26}N_6O_3$ (374.45)
Rf=0.27 (dichloromethane/methanol/ammonia 85/13/2)

EXAMPLE 25

6-[4-(2-acetamidoethyl)amino-3-nitro-phenyl]-4,5-dihydro-5-methyl-3(2H)-pyridazinone

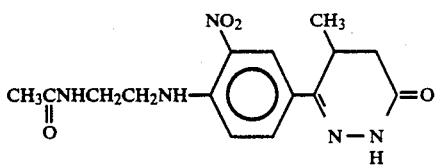

0.40 ml (4.23 mmol) of acetic anhydride is added to a solution of 1.00 g (3.43 mmol) of 6-[4-(2-aminoethyl-)amino-3-nitro-phenyl]-4,5-dihydro-5-methyl-3(2H)-pyridazinone in 10 ml of glacial acetic acid and the solution is stirred at room temperature for 20 hours. The precipitated solid is suction filtered and washed with 5 ml of dichloromethane. The mother liquor is concentrated by evaporation under vacuum and the residue obtained is stirred up with 5 ml of dichloromethane and filtered. The two crystal fractions are recrystallized together from ethanol (99.7%). 0.86 g (75%) of orange coloured crystals, m.p. 222° C., are obtained.

$C_{15}H_{19}N_5O_4$ (333.35)

Rf=0.60 (dichloromethane/methanol 90/10)

EXAMPLE 26

6-[4-(4-ethoxycarbonyl-piperazin-1-yl)-3-nitro-phenyl]-4,5-dihydro-5-hydroxymethyl-3(2H)-pyridazinone

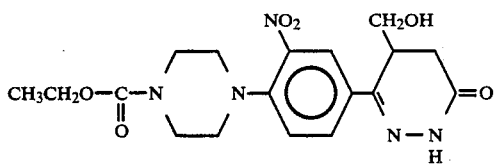

(a) 4-(4-chloro-3-nitro-benzoyl)-tetrahydrofuran-2-one 3.37 g (15 mmol) of 4-(4-chlorobenzoyl)-tetrahydrofuran-2-one are added portion wise to 30 ml of nitric acid (100%) at −15° C. The temperature should not exceed −5° C. Stirring is continued for 30 minutes after all the compound has been added and the mixture is then poured out on 300 ml of ice water and the solid which has precipitated is separated by suction filtration and washed with water.

The filter cake is recrystallized from 100 ml of ethanol. 3.26 g (80% of theoretical) of almost colourless crystals, m.p. 118° to 120° C., are obtained.

$C_{11}H_8ClNO_5$ (269.64)

Rf=0.36 (ethyl acetate/petroleum ether 60/40)

(b) 6-(4-chloro-3-nitro-phenyl)-4,5-dihydro-5-hydroxymethyl-3(2H)-pyridazinone 21.6 g (0.08 mol) of the tetrahydrofuranone obtained as under (a) and 25 ml (0.4 mol) of hydrazine hydrate (80% in water) are stirred together in 200 ml of glacial acetic acid at 80° C. for two hours. The reaction mixture is left to cool and stirred into an ice bath to complete crystallization. 20.5 g (82% of theoretical) of a slightly yellowish solid melting at 236° to 238° C. are obtained after suction filtration.

$C_{11}H_{10}ClN_3O_4$ (283.67)

Rf=0.41 (dichloromethane/methanol 95/5)

(c) 6-[4-(4-ethoxycarbonyl-piperazin-1-yl)-3-nitro-phenyl]-4,5-dihydro-5-hydroxymethyl-3(2H)-pyridazinone 3.12 g (10 mmol) of the pyridazinone from stage (b) are reacted with 7.91 g (50 mmol) of 1-ethoxycarbonyl-piperazine in a manner analogous to Example 1.

After recrystallization of the crude product from ethanol, 2.0 g (49% of theoretical) of an orange coloured powder, m.p. 163.5°–164° C., are obtained.

$C_{18}H_{23}N_5O_6$ (405.41)

Rf=0.30 (ethyl acetate/methanol 95/5)

EXAMPLE 27

6-[3-nitro-4-(1-piperazinyl)-phenyl]-4,5-dihydro-5-hydroxymethyl-3(2H)-pyridazinone

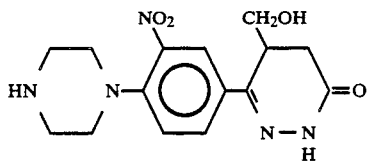

19.86 g (0.07 mol) of 6-(4-chloro-3-nitro-phenyl)-4,5-dihydro-5-hydroxymethyl-3(2H)-pyridazinone are reacted with 18.1 g (0.21 mol) of piperazine in a manner analogous to Example 1.

16.17 g (69% of theoretical) of an orange red powder, m.p. 182° to 184° C., are obtained after recrystallization from ethanol.

$C_{15}H_{19}N_5O_4$ (333.35)

Rf=0.1 (ethyl acetate/methanol/NH$_3$ 80/12/2)

EXAMPLE 28

6-[3-cyano-4-(4-ethoxycarbonyl-piperazin-1-yl)phenyl]-4,5-dihydro-5-methyl-3(2H)-pyridazinone

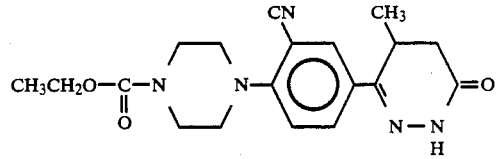

(a) 6-(4-chloro-3-cyano-phenyl)-4,5-dihydro-5-methyl-3(2H)-pyridazinone

A suspension of 5.0 g (21 mmol) of 6-(3-amino-4-chlorophenyl)-4,5-dihydro-5-methyl-3(2H)-pyridazinone in 160 ml of water and 16 ml of conc. hydrochloric acid is diazotised with a solution of 1.5 g (21 mmol) of sodium nitrite in 10 ml of water at 0° C. The diazonium salt solution is then neutralized with K$_2$CO$_3$ and added portionwise at 0° C. to a thoroughly stirred solution of 2.8 g (31.5 mmol) of CuCN and 6.3 g (96 mmol) of KCN in 100 ml of water. The reaction mixture is then left to warm up to room temperature and the solid which precipitates is separated by suction filtration after 12 hours. The filtrate is extracted with CHCl$_3$/CH$_3$OH (80/20 vv), the organic phase is concentrated by evaporation and the residue is combined with the filter cake. After recrystallization from methanol, 2.6 g (50% of theoretical) of colourless crystals, m.p. 208°–209.5° C., are obtained.

$C_{12}H_{10}N_3ClO$ (247.68)

Rf=0.62 (dichloromethane/methanol 95/5)

(b)
6-[3-cyano-4-(4-ethoxycarbonyl-piperazin-1-yl)phenyl]-4,5-dihydro-5-methyl-3(2H)-pyridazinone 1.5 g (6.1 mmol) of the chlorocyanophenylpyridazinone from stage (a) and 5 ml of 1-ethoxycarbonylpiperazine are together heated to 170° C. for 5 hours. After the reaction mixture has cooled, it is poured out on water and extracted with ethyl acetate and the combined organic phases are concentrated by evaporation under vacuum.

The residue is chromatographed on silica gel (solvent: dichloromethane/methanol 96/4). The main fractions are combined and the residue is crystallized from a small quantity of ethanol (99.7%).

0.8 g (35% of theoretical) of colourless crystals, m.p. 146.0°-146.6° C., are obtained.

$C_{19}H_{23}N_5O_3$ (369.43)
Rf=0.50 (dichloromethane/methanol 95/5)

EXAMPLE 29

6-[4-(4-aminomethyl-piperidin-1-yl)-3-nitro-phenyl]-4,5-dihydro-5-methyl-3(2H)-pyridazinone

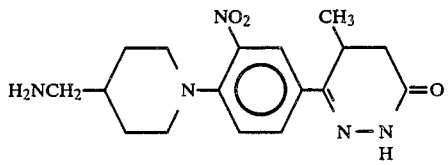

(a)
6-[4-(4-phthalimidomethyl-piperidin-1-yl)-3-nitro-phenyl]-4,5-dihydro-5-methyl-3(2H)-pyridazinone 2.68 g (10 mmol) of 6-(4-chloro-3-nitro-phenyl)-4,5-dihydro-5-methyl-3(2H)-pyridazinone and 2.81 g (10 mmol) of 4-phthalimidomethyl-piperidine hydrochloride are suspended in 30 ml of dioxane. After the addition of 2.8 ml (20 mmol) of triethylamine, the mixture is boiled under reflux for 4 hours. After it has cooled to room temperature, the solution is filtered from the residue and concentrated by evaporation under vacuum. After recrystallization of the solid residue from acetonitrile, 3.76 g (79%) of an orange yellow solid, m.p. 256°-258° C., are obtained.

$C_{25}H_{25}N_5O_5$ (475.51)
Rf=0.45 (dichloromethane/methanol 95/5)

(b)
6-[4-(4-aminomethyl-piperidin-1-yl)-3-nitrophenyl]-4,5-dihydro-5-methyl-3(2H)-pyridazinone 3.0 g (6.3 mmol) of the phthalimido compound from stage (a) and 1.5 ml (33.3 mmol) of hydrazine hydrate (99%) are boiled under reflux in 50 ml of ethanol for 2 hours. After the reaction mixture has cooled to room temperature, it is filtered and the filtrate is concentrated by evaporation under vacuum. The residue obtained is taken up with 20 ml of water and the solution is adjusted to pH 1 with 2N hydrochloric acid and again filtered. The filtrate obtained is adjusted to pH 10 with conc. ammonia. An orange yellow solid then precipitates, which is suction filtered and recrystallized from acetonitrile/ethanol (7:1). 1.16 g (53%) of an orange yellow solid, m.p. 131° to 132° C. are obtained.

$C_{17}H_{23}N_5O_3$ (345.40)

Rf=0.57 (ethyl acetate/ethanol/conc. ammonia 15/10/2)

EXAMPLE 30

6-[4-[4-(4-aminobutyl)-piperazin-1-yl]-3-nitro-phenyl]-5-methyl-4,5-dihydro-3(2H)-pyridazinone

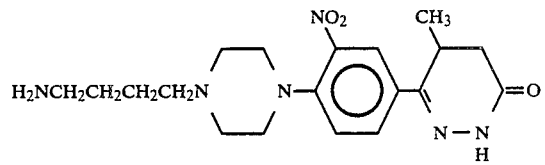

(a)
5-methyl-6-[3-nitro-4-[4-(1-phthalimido)butyl]-piperazin-1-yl]phenyl]-4,5-dihydro-3(2H)-pyridazinone 5.6 g (17.7 mmol) of 5-methyl-6-[3-nitro-4-(1-piperazinyl)phenyl]-4,5-dihydro-3(2H)-pyridazinone are reacted with 5.0 g of N-(4-bromobutyl)-phthalimide in a manner analogous to Example 24(a). 6.94 g (76% of theoretical) of an orange coloured powder, m.p. 179°-180° C., are obtained.

$C_{27}H_{30}N_6O_5$ (518.58)
Rf=0.62 (ethyl acetate/methanol/ammonia 80/18/2)

(b)
6-[4-[4-(4-aminobutyl)-piperazin-1-yl]-3-nitro-phenyl]-5-methyl-4,5-dihydro-3(2H)-pyridazinone 6.64 g (12.8 mmol) of the compound obtained under (a) are reacted with 1.92 g (38.6 mmol) of hydrazine hydrate (99%) in a manner analogous to Example 24(b).

The yield of the title compound obtained in the form of orange crystals of melting point 145°-146° C. is 4.2 g (85% of theoretical).

$C_{19}H_{28}N_6O_3$ (388.47)
Rf=0.28 (dichloromethane/methanol/ammonia 85/13/2)

EXAMPLE 31

6-[3-cyano-4-(1-piperazinyl)phenyl]-4,5-dihydro-5-methyl-3(2H)-pyridazinone

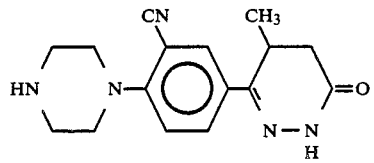

10.0 g (40.4 mmol) of 6-(4-chloro-3-cyano-phenyl)-4,5-dihydro-5-methyl-3(2H)-pyridazinone are reacted with 10 g of piperazine in a manner analogous to Example 1.

Recrystallization from ethanol yields 9.8 g (82% of theoretical) of a colourless powder of m.p. 188°-189° C.

$C_{16}H_{19}N_5O$ (297.36)
Rf=0.37 (dichloromethane/methanol/ammonia 85/13/2)

EXAMPLE 32

6-[4-(4-aminopiperidin-1-yl)-3-nitro-phenyl]-5-methyl-4,5-dihydro-3(2H)-pyridazinone

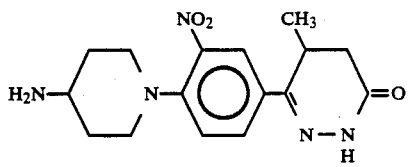

3.5 g (13 mmol) of 4-(4-chloro-3-nitro-phenyl)-5-methyl-4,5-dihydro-3(2H)-pyridazinone are boiled under reflux with 3.0 g (13 mmol) of 4-(1-phthalimido)-piperidine and 4 ml of pyridine in 100 ml of dioxane for 8 hours.

The dioxane is distilled off under vacuum, 100 ml of ethanol and 3.2 ml of hydrazine hydrate are added to the residue and the mixture is heated under reflux for a further 3 hours.

Water is then added and the mixture is made strongly alkaline with NaOH solution (pH 12).

After extraction with chloroform and evaporation of the solvent under vacuum, a dark brown oil is left behind which is chromatographed on silica gel (solvent: ethyl acetate/methanol/$NH_3$ 80/18/2).

The main fractions are combined and concentrated by evaporation and the residue is recrystallized from methanol. 560 mg (13% of theoretical) of the title compound are obtained as orange crystals, m.p. 151° to 153° C.

$C_{16}H_{21}N_5O_3$ (331.38)

Rf=0.12 (ethyl acetate/methanol/ammonia 80/18/2)

EXAMPLE 33

6-[3-nitro-4-[4-[4-(1-phthalimido)butyryl]piperazin-1-yl]phenyl]-5-methyl-4,5-dihydro-3(2H)-pyridazinone

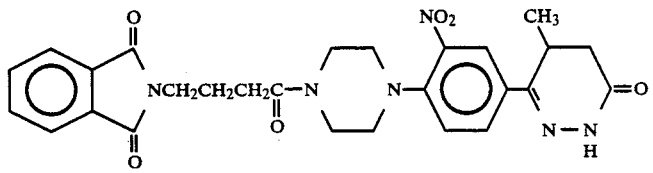

8.0 g (31.8 mmol) of 4-(1-phthalimido)-butyric acid chloride are rapidly added dropwise to a slurry of 10.9 g (31.5 mmol) of 5-methyl-6-[3-nitro-4-(1-piperazinyl)-phenyl]-4,5-dihydro-3(2H)-pyridazinone in 80 ml of pyridine.

After 8 hours at room temperature, the reaction mixture is poured out on 700 ml of water, stirred for a further 2 hours at room temperature and suction filtered to separate the solid, and the filter cake is washed with water.

After drying under vacuum, the title compound is obtained in a yield of 14.4 g (86% of theoretical) as a yellow powder melting at 125°-126° C.

$C_{27}H_{28}N_7O_6$ (532.56)

Rf=0.63 (ethyl acetate/methanol/ammonia 80/18/2)

EXAMPLE 34

6-[3-amino-4-[4-(2-pyrimidyl)-piperazin-1-yl]phenyl]-4,5-dihydro-5-methyl-3(2H)-pyridazinone

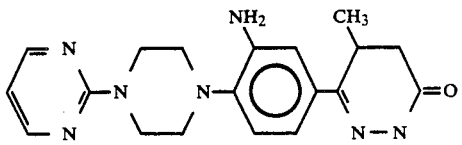

2.5 g (6.3 mmol) of 6-[3-nitro-4[4-(2-pyrimidyl)-piperazin-1-yl]-phenyl]-4,5-dihydro-5-methyl-3(2H)-pyridazinone in 130 ml of methanol are hydrogenated under a hydrogen pressure of 5 bar in the presence of 0.3 g of palladium on active charcoal (10% Pd) at 50° C. for 3 hours. After removal of the catalyst by suction filtration, the filtrate is highly concentrated by evaporation under vacuum and the residue obtained is chromatographed on silica gel, using dichloromethane/methanol (95:5) as solvent. After concentration of the product fractions by evaporation, the residue obtained is crystallized with acetone. 0.70 g (30%) of pale beige crystals, m.p. 220° to 221° C., are obtained.

$C_{19}H_{23}N_7O$ (365.44)

Rf=0.15 (dichloromethane/methanol 95/5)

EXAMPLE 35

6-[3-fluoro-4-(piperazin-1-yl)-phenyl]-4,5-dihydro-5-methyl-3(2H)-pyridazinone

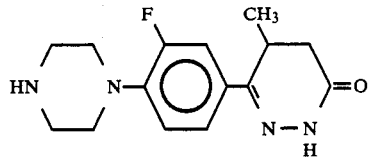

5.0 g (22.3 mmol) of 6-(3,4-difluorophenyl)-4,5-dihydro-5-methyl-3(2H)-pyridazinone and 19.2 g (222 mmol) of piperazine are stirred at 160° C. for 15 hours. When the reaction mixture has cooled down, it is taken up with 200 ml of dichloromethane and washed with 3×30 ml of water. After drying, the organic phase is concentrated by evaporation and the residue is crystallized with methanol. The solid obtained is suction filtered and recrystallized from ethyl acetate. 3.5 g (54%) of colourless crystals, m.p. 172°-174° C., are obtained.

$C_{15}H_{19}FN_4O$ (290.34)

Rf=0.53 (methanol/conc. ammonia 95/5)

EXAMPLE 36

6-[4-(4-ethoxycarbonyl-piperazin-1-yl)-3-fluoro-phenyl]-4,5-dihydro-5-methyl-3(2H)-pyridazinone

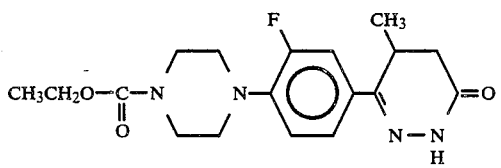

1.2 g (8.6 mmol) of potassium carbonate are added to a solution of 1.0 g (3.4 mmol) of 6-[3-fluoro-4-(piperazin-1-yl)-phenyl]-4,5-dihydro-5-methyl-3(2H)-pyridazinone in 10 ml of acetone and 10 ml of water. When the suspension has cooled down to 0° C., 0.42 ml (4.4 mmol) of ethyl chloroformate are added and stirring is continued for 30 minutes. The precipitated solid is suction filtered, washed with 10 ml of acetone-water mixture and recrystallized from 40 ml of acetonitrile. 0.73 g (60%) of a colourless solid, m.p. 193°–194° C., are obtained.

$C_{18}H_{23}FN_4O_3$ (362.41)

Rf=0.40 (dichloromethane/methanol 95/5)

EXAMPLE 37

6-[4-[(3-aminopropyl)amino]-3-nitro-phenyl]-4,5-dihydro-5-hydroxymethyl-3(2H)-pyridazinone

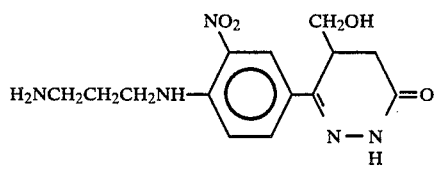

14.0 g (50 mmol) of 6-(4-chloro-3-nitro-phenyl)-4,5-dihydro-5-hydroxymethyl-3(2H)-pyridazinone are heated to 60° C. together with 50 ml of 1,3-diaminopropane in 40 ml of dioxane for 8 hours.

The reaction mixture is then poured out on 200 ml of ice water and left to crystallize with cooling.

After suction filtration and washing of the filter cake with water and ethanol, an orange coloured solid melting at 180° to 181° C. is obtained in a yield of 14.05 g (87% of theoretical).

$C_{14}H_{19}N_5O_4$ (321.34)

Rf=0.17 (dichloromethane/methanol/NH3 85/13/2)

We claim:

1. A 6-(4-piperazino)-phenyl-4,5-dihydro-3(2H)-pyridazinone, comprising

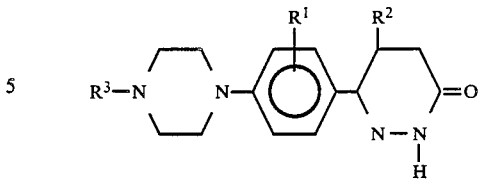

wherein $R^1$ is nitro or cyano; $R^2$ is selected from the group consisting of hydrogen, methyl and hydroxymethyl and $R^3$ is selected from the group consisting of a $C_1$–$C_6$ alkyl group, a $C_1$–$C_6$ alkyl group substituted with amino or hydroxy, a phenyl group, a naphthyl group, a heteroaryl group wherein the hetero atom is selected from the group consisting of O, S and N, a substituted such aryl or heteroaryl group wherein the substituents are selected from the group consisting of halogen, $C_1$–$C_3$ alkyl and $C_1$–$C_3$ alkoxy, a cyano group, an acyl group with the proviso that, when said acyl group is aroyl, the aroyl ring may be substituted with substituents selected from the group consisting of halogen, $C_1$–$C_3$ alkyl and $C_1$–$C_3$ alkoxy, a carbonyl group and a $C_1$–$C_6$ alkoxycarbonyl group, and a physiologically acceptable salt thereof.

2. A 6-Phenyldihydro-3(2H)-pyridazinone corresponding to the formula

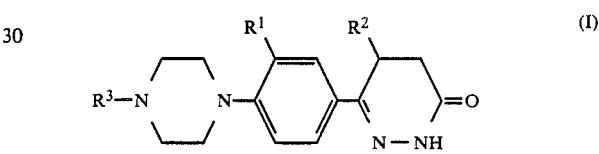

in which $R^1$ denotes a nitro or a cyano group, $R^2$ denotes a hydrogen atom or a methyl group and $R^3$ stands for an ethoxycarbonyl or an acetyl group, and the physiologically acceptable salts thereof.

3. A 6-phenyldihydro-3(2H)-pyridazinone according to claim 2, consisting of 6-[4-(4-ethoxycarbonyl-piperazin-1-yl)-3-nitro-phenyl]-4,5-dihydro-5-methyl-3(2H)-pyridazinone.

4. A 6-phenyldihydro-3(2H)-pyridazinone according to claim 2, consisting of 6-[4-(4-ethoxycarbonyl-piperazin-1-yl)-3-nitro-phenyl]-4,5-dihydro-3(2H)-pyridazinone.

5. A 6-phenyldihydro-3(2H)-pyridazinone according to claim 2, consisting of 6-[4-(4-acetyl-piperazin-1-yl)-3-nitro-phenyl]-5-methyl-4,5-dihydro-3(2H)-pyridazinone.

6. A 6-phenyldihydro-3(2H)-pyridazinone according to claim 2, consisting of 6-[3-cyano-4-(4-ethoxycarbonyl-piperazin-1-yl)phenyl]-4,5-dihydro-5-methyl-3(2H)-pyridazinone.

7. Pharmaceutical preparation, characterised in that it contains a compound according to claim 2 together with at least one inert, pharmaceutically acceptable carrier or diluent.

* * * * *